United States Patent
Eng (10) Patent No.: US 8,674,155 B2
(45) Date of Patent: Mar. 18, 2014

(54) SYSTEMS AND METHODS FOR PROCESSING HYDROCARBONS

(75) Inventor: Curtis N. Eng, Sugar Land, TX (US)

(73) Assignee: Kellogg Brown & Root, LLC, Houston, TX (US)

( * ) Notice: Subject to any disclaimer, the term of this patent is extended or adjusted under 35 U.S.C. 154(b) by 72 days.

(21) Appl. No.: 12/975,767

(22) Filed: Dec. 22, 2010

(65) Prior Publication Data

US 2012/0165584 A1   Jun. 28, 2012

(51) Int. Cl.
C07C 6/00 (2006.01)
C07C 6/02 (2006.01)
C07C 6/04 (2006.01)

(52) U.S. Cl.
USPC ............ 585/324; 585/643; 585/646; 585/647

(58) Field of Classification Search
USPC ......... 585/250, 251, 271, 310, 324, 500, 634, 585/643, 648
See application file for complete search history.

(56) References Cited

U.S. PATENT DOCUMENTS

| | | | |
|---|---|---|---|
| 5,811,621 A | 9/1998 | Van Dijk | |
| 6,580,009 B2 * | 6/2003 | Schwab et al. | 585/324 |
| 6,602,920 B2 | 8/2003 | Hall et al. | |
| 7,183,451 B2 | 2/2007 | Gattis et al. | |
| 7,208,647 B2 | 4/2007 | Peterson et al. | |
| 7,223,895 B2 | 5/2007 | Sumner | |
| 7,408,091 B2 | 8/2008 | Johnson et al. | |
| 7,525,007 B2 | 4/2009 | Sumner | |
| 2002/0007101 A1 | 1/2002 | Senetar et al. | |
| 2005/0033103 A1 | 2/2005 | Van Egmond et al. | |
| 2005/0033104 A1 | 2/2005 | Van Egmond et al. | |
| 2005/0065391 A1 * | 3/2005 | Gattis et al. | 585/943 |
| 2005/0107650 A1 | 5/2005 | Sumner | |
| 2007/0135668 A1 | 6/2007 | Sumner | |
| 2008/0146856 A1 | 6/2008 | Leyshon et al. | |
| 2008/0200745 A1 * | 8/2008 | Sigl et al. | 585/643 |
| 2009/0198090 A1 | 8/2009 | Mamedov et al. | |
| 2010/0087686 A1 | 4/2010 | Fong et al. | |

OTHER PUBLICATIONS

Gannon, et al., "Acetylene from Hydrocarbons" in Kirk-Othmer Encyclopedia of Chemical Technology, 2003, John Wiley & Sons, available on-line Apr. 18, 2003.*
Sundaram, et al., "Ethylene" in Kirk-Othmer Encyclopedia of Chemical Technology, 2003, John Wiley & Sons, available on-line Apr. 18, 2003.*
Weissermel et al. Olefins. Industrial Organic Chemistry. 2008. pp. p. 68.*
Kenneth R. Hall et al., A New Process for Converting Natural Gas into Hydrocarbon Liquids, technical paper, Mar. 31, 2003, pp. 18-26, Unpublished, Chemical Engineering Dept., Texas A&M University, College Station, TX.
Robert J. Gartside, et al., Integrating CPT With Existing OCT Units, Power Point presentation, Apr. 2008, 20th Ethylene Producers Conference, New Orleans, LA.
Robert J. Gartside, et al., ABB's Olefin Vision 2010, Presentation, Mar. 11, 2002, 2002 AIChE Spring National Meeting, New Orleans, LA.
Jean Paul Laugier, Article 86A, Metathesis—An Enhanced Propylene Production, Case Study, 2010, Houston, TX.
Chemsystems Perp Program, Gas to Ethylene PERP 08/09S10, Nexant, Sep. 2009, White Plains, New York.

* cited by examiner

Primary Examiner — Walter D Griffin
Assistant Examiner — Jelitza Perez
(74) Attorney, Agent, or Firm — Gary M. Machetta (57) ABSTRACT

Systems and methods for processing one or more hydrocarbons are provided. In one or more embodiments, the method can include thermally converting a hydrocarbon comprising methane to produce a first product comprising acetylene. The method can also include hydrogenating the first product to produce a second product comprising ethylene. The method can further include catalytically reacting the second product with one or more butene products to produce a third product comprising propylene.

20 Claims, 2 Drawing Sheets

SYSTEMS AND METHODS FOR PROCESSING HYDROCARBONS

BACKGROUND

1. Field

Embodiments described herein generally relate to systems and methods for processing hydrocarbons. More particularly, such embodiments relate to systems and methods for producing propylene.

2. Description of the Related Art

An abundance of natural gas exists throughout the world. The natural gas can be converted directly into hydrocarbon liquids, for example olefins via intermediate products, such as Fischer-Tropsch liquids or methanol. Fischer-Tropsch liquids are produced in a Fischer-Tropsch process by first converting natural gas to a synthesis gas that is a mixture of carbon monoxide and hydrogen and then converting the synthesis gas into liquid and solid hydrocarbons having both paraffins and olefins. Byproducts of the process can include ethylene and propylene. Producing propylene using methanol or Fischer-Tropsch processes, however, is relatively inefficient, can be complicated, and can require a multiplicity of units to operate effectively leading to high expense.

There is a need, therefore, for improved systems and methods for converting natural gas to propylene.

DETAILED DESCRIPTION

Systems and methods for processing one or more hydrocarbons are provided. In one or more embodiments, the method can include thermally converting a hydrocarbon comprising methane to produce a first product comprising acetylene. The method can also include hydrogenating the first product to produce a second product comprising ethylene. The method can further include catalytically reacting the second product with one or more butene products to produce a third product comprising propylene.

Figure 1:
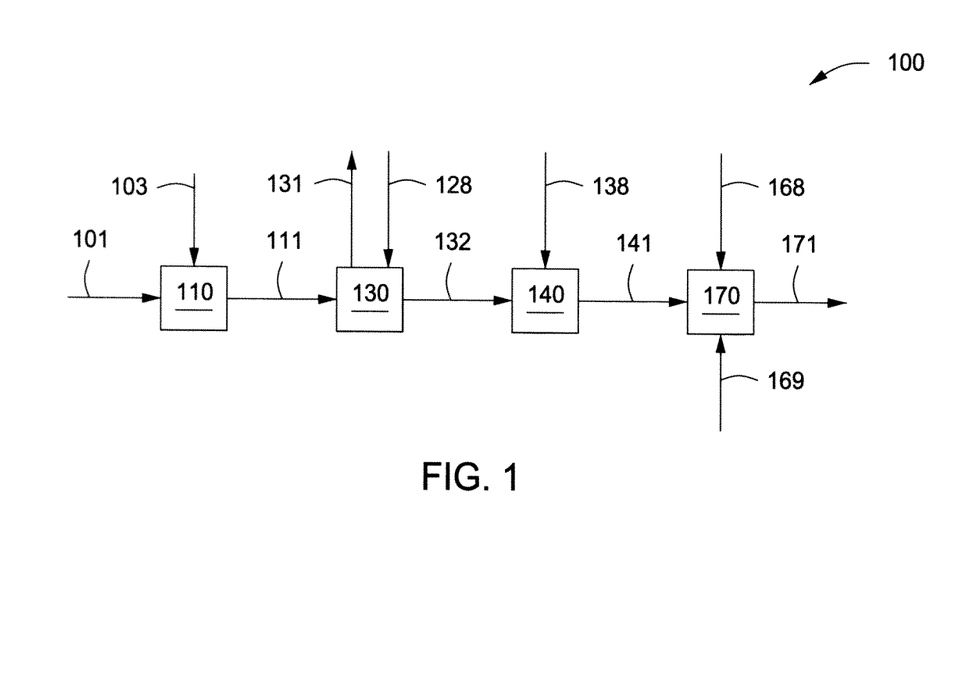
FIG. 1 depicts a schematic of an illustrative system for converting methane to propylene, according to one or more embodiments described.

FIG. 1 depicts a schematic of an illustrative system 100 for converting methane to propylene, according to one or more embodiments. In one or more embodiments, the system 100 can include one or more first reactors or "crackers" 110, one or more non-acetylene removal units 130, one or more second or "hydrogenation" reactors or "hydrogenators" 140, and one or more third or "metathesis" reactors 170. The one or more crackers 110 can be in fluid communications with the one or more non-acetylene removal units 130 via at least line 111. The one or more non-acetylene removal units 130 can be in fluid communications with the one or more hydrogenators 140 via at least line 132. The one or more hydrogenators 140 can be in fluid communications with the one or more metathesis reactors 170 via at least line 141.

One or more hydrocarbons containing some amount of methane can be introduced via line 101 and oxygen can be introduced via line 103 to the one or more reactors 110 to produce a first effluent via line 111. At least a portion of the hydrocarbon introduced via line 101 can be converted in the first reactor 110 to acetylene, ethylene, hydrogen, carbon monoxide, carbon dioxide water, oxygen, nitrogen, or any combination thereof. In at least one embodiment, a first portion of the hydrocarbon via line 101 can be combusted to produce heat. The heat can be indirectly transferred to a second portion of the hydrocarbon within the first reactor 110 to at least partially convert the hydrocarbon to produce the first effluent via line 111.

The reactor 110 can be a partial oxidation cracker, a pyrolysis cracker, a thermal cracker, or other commonly used methane cracking methods. The reactor 110 can also use catalysts to convert methane, such as in fixed beds, moving beds, fluid beds, or similar reactor types. When the reactor 110 is a partial oxidation cracker, the hydrocarbon via line 101 and the oxygen via line 103 can be co-fed to the reactor 110 in a sub-stoichiometric ratio.

The hydrocarbon via line 101 can be at ambient temperature and pressure conditions and can include, but is not limited to, one or more $C_1$ to $C_{12}$ hydrocarbons, carbon dioxide, or any combination thereof. For example, the hydrocarbon via line 101 can include methane, ethane, propane, butane, pentane, hexane, carbon dioxide, $C_4$ or heavier hydrocarbons, or any combination thereof. The hydrocarbon via line 101 can have a methane concentration ranging from a low of about 75 percent by mole (mol %), about 77 mol %, about 79 mol %, or about 85 mol % to a high of about 90 mol %, about 96 mol %, about 98 mol %, or about 100 mol %. For example, the hydrocarbon via line 101 can have a methane concentration of from about 76 mol % to about 99 mol %, about 78 mol % to about 97 mol %, or about 80 mol % to about 95 mol %. The hydrocarbon via line 101 can have an ethane concentration ranging from a low of about 0 mol %, about 2 mol %, about 4 mol %, or about 6 mol % to a high of about 9 mol %, about 11 mol %, about 13 mol %, or about 15 mol %. For example, the hydrocarbon via line 101 can have an ethane concentration of from about 1 mol % to about 14 mol %, about 3 mol % to about 12 mol %, or about 5 mol % to about 10 mol %. The hydrocarbon via line 101 can have a propane concentration ranging from a low of about 0 mol %, about 2 mol %, or about 4 mol % to a high of about 6 mol %, about 8 mol %, or about 10 mol %. For example, the hydrocarbon via line 101 can have a propane concentration of from about 1 mol % to about 9 mol % or about 3 mol % to about 7 mol %. The hydrocarbon via line 101 can have a carbon dioxide concentration ranging from a low of about 0 mol %, about 2 mol %, about 4 mol %, or about 6 mol % to a high of about 9 mol %, about 11 mol %, about 13 mol %, or about 15 mol %. For example, the hydrocarbon via line 101 can have a carbon dioxide concentration of from about 1 mol % to about 14 mol %, about 3 mol % to about 12 mol %, or about 5 mol % to about 10 mol %. The hydrocarbon via line 101 can have from a low of about 0 mol %, about 2 mol %, or about 4 mol % to a high of about 6 mol %, about 8 mol %, or about 10 mol % $C_4$ or heavier hydrocarbons. For example, the hydrocarbon via line 101 can have of from about 1 mol % to about 9 mol %, about 3 mol % to about 7 mol %, or about 5 mol % to about 7 mol % $C_4$ or heavier hydrocarbons.

The first effluent via line 111 can include, but is not limited to, acetylene, hydrogen, carbon monoxide, carbon dioxide, water, or any combination thereof. The first effluent via line 111 can have an acetylene concentration ranging from a low of about 5 mol %, about 7 mol %, or about 9 mol % to a high of about 11 mol %, about 13 mol %, or about 15 mol %. For example, the effluent via line 111 can have an acetylene concentration of from about 6 mol % to about 14 mol % or about 8 mol % to about 12 mol %. The first effluent via line 111 can have a hydrogen concentration ranging from a low of about 20 mol %, about 25 mol %, or about 30 mol % to a high of about 40 mol %, about 45%, or about 50 mol %. For example, the first effluent via line 111 can have a hydrogen concentration of from about 23 mol % to about 47 mol % or about, 26 mol % to about 44 mol %, or about 27 mol % to about 43 mol %. The first effluent via line 111 can have a carbon monoxide concentration ranging from a low of about 5 mol %, about 7 mol %, about 9 mol %, or about 11 mol % to a high of about 14 mol %, about 16 mol %, about 18 mol %, or about 20 mol %. For example, first effluent via line 111 can have a carbon monoxide concentration of from about 6 mol % to about 19 mol %, about 8 mol % to about 17 mol %, or about 10 mol % to about 15 mol %. The first effluent via line 111 can have a carbon dioxide concentration ranging from a low of about 1 mol %, about 2 mol %, or about 3 mol % to a high of about 4 mol % or about 5 mol %. The first effluent via line 111 can have a water concentration ranging from a low of about 30 mol %, about 32 mol %, about 34 mol %, or about 36 mol % to a high of about 44 mol %, about 46 mol %, about 48 mol %, or about 50 mol %. For example, first effluent via line 111 can have a water concentration of from about 31 mol % to about 49 mol %, about 33 mol % to about 47 mol %, or about 35 mol % to about 45 mol %. The first effluent via line 111 can have a nitrogen concentration of about 2 mol % or less or about 1 mol % or less. The first effluent via line 111 can have an oxygen concentration of about 2 mol % or less or about 1 mol % or less.

The first effluent via line 111 can have temperature of about 520° C. or more, about 530° C. or more, about 540° C. or more, about 550° C. or more, or about 560° C. or more, or about 600° C. or more. The first effluent via line 111 can have a pressure ranging from a low of about 135 kPa, about 140 kPa, about 145 kPa, or about 150 kPa to a high of about 155 kPa, about 160 kPa, about 165 kPa, or about 170 kPa. For example, the first effluent via line 111 can have a pressure of from about 137 kPa to about 168 kPa, about 143 kPa to about 162 kPa, or about 147 kPa to about 158 kPa.

The first effluent via line 111 can be introduced to the one or more non-acetylene removal units 130 to separate acetylene from the first effluent via line 111, producing a second or "acetylene-lean" effluent via line 131 and a third or "acetylene-rich" effluent via line 132.

Separation of the acetylene in the non-acetylene removal unit 130 can be performed according to known methods including, but not limited to, absorption, distillation, selective membrane permeation, pressure swing absorption, or other separation techniques known in the art. When absorption is used in the non-acetylene removal unit 130, a solvent can be introduced via line 128 to one or more columns (not shown) of the non-acetylene removal unit 130 to flow counter-current to the flow of the first effluent via line 111. The solvent via line 128 can contact the effluent via line 111 to produce the acetylene-rich effluent via line 132 at a bottom of the one or more columns (not shown) and the acetylene-lean effluent via line 131. The acetylene-lean effluent via line 131 can be a syngas that can be used for further processing. Although not shown, the acetylene-lean effluent via line 131 can be recycled to the reactor 110. The solvent 128 can include, but is not limited to, N-Methyl Pyrrolidone ("NMP").

The second effluent via line 131 can include, but is not limited to, methane, acetylene, hydrogen, carbon monoxide, carbon dioxide, oxygen, nitrogen, $C_2$ hydrocarbons, or any combination thereof. The second effluent via line 131 can haven methane concentration ranging from a low of about 0 percent by weight (wt %), about 2 wt %, or about 4 wt % to a high of about 6 wt %, about 8 wt %, or about 10 wt %. For example, the second effluent via line 131 can have a methane concentration of from about 1 wt % to about 9 wt % or about 3 wt % to about 7 wt %. The second effluent via line 131 can have a carbon dioxide concentration ranging from a low of about 5 wt %, about 7 wt %, about 10 wt %, or about 13 wt % to a high of about 17 wt %, about 20 wt %, about 23 wt %, or about 25 wt %. For example, the second effluent via line 131 can have a carbon dioxide concentration of from about 6 wt % to about 24 wt %, about 8 wt % to about 22 wt %, or about 12 wt % to about 18 wt %. The second effluent via line 131 can have a nitrogen concentration ranging from a low of about 1 wt %, about 3 wt %, or about 5 wt % to a high of about 6 wt %, about 8 wt %, or about 10 wt %. For example, the second effluent via line 131 can have a nitrogen concentration of from about 2 wt % to about 9 wt % or about 4 wt % to about 7 wt %. The second effluent via line 131 can have a hydrogen concentration ranging from a low of about 5 wt %, about 7 wt %, or about 9 wt % to a high of about 11 wt %, about 13 wt %, or about 15 wt %. For example, the second effluent via line 131 can have a hydrogen concentration of from about 6 wt % to about 14 wt % or about 8 wt % to about 12 wt %. The second effluent via line 131 can have a carbon monoxide concentration ranging from a low of about 40 wt %, about 45 wt %, about 50 wt %, or about 55 wt % to a high of about 65 wt %, about 70 wt %, about 75 wt %, or about 80 wt %. For example, second effluent via line 131 can have a carbon monoxide concentration of from about 43 wt % to about 77 wt %, about 48 wt % to about 72 wt %, or about 53 wt % to about 67 wt %. The second effluent via line 131 can have an oxygen concentration of about 2 wt % or less or about 1 wt % or less. The second effluent via line 131 can include about 5 wt % or less, about 4 wt % or less, about 3 wt % or less, about 2 wt % or less, or about 1 wt % or less $C_2$ hydrocarbons.

The second effluent via line 131 can exit the non-acetylene removal unit 130 at ambient temperature and a low pressure. For example, the second effluent via line 131 can exit the non-acetylene removal unit 130 at a pressure ranging from a low of about 135 kPa, about 140 kPa, about 145 kPa, or about 150 kPa to a high of about 155 kPa, about 160 kPa, about 165 kPa, or about 170 kPa. In another example, the second effluent via line 131 can exit the non-acetylene removal unit 130 at a pressure of from about 137 kPa to about 168 kPa, about 143 kPa to about 162 kPa, or about 147 kPa to about 158 kPa.

The third effluent via line 132 can include acetylene, methane, carbon dioxide, solvent, or any combination thereof. The acetylene in the third effluent via line 132 can be at least partially contained in the solvent. The third effluent via line 132 can have an acetylene concentration ranging from a low of about 5 wt %, about 10 wt %, about 15 wt %, or about 20 wt % to a high of about 35 wt %, about 40 wt %, about 45 wt %, or about 50 wt %. For example, the third effluent via line 132 can have an acetylene concentration of from about 7 wt % to about 48 wt %, about 12 wt % to about 43 wt %, or about 17 wt % to about 38 wt %. The third effluent via line 132 can have a methane concentration ranging from a low of about 1 wt %, about 3 wt %, or about 5 wt % to a high of about 6 wt %, about 8 wt %, or about 10 wt %. For example, the third effluent via line 132 can have a methane concentration of from about 2 wt % to about 9 wt % or about 4 wt % to about 7 wt %. The third effluent via line 132 can have a carbon dioxide concentration ranging from a low of about 1 wt %, about 3 wt %, or about 5 wt % to a high of about 6 wt %, about 8 wt %, or about 10 wt %. For example, the third effluent via line 132 can have a carbon dioxide concentration of from about 2 wt % to about 9 wt % or about 4 wt % to about 7 wt %. The third effluent via line 132 can have a solvent concentration ranging from a low of about 30 wt %, about 35 wt %, about 40 wt %, or about 45 wt % to a high of about 80 wt %, about 85 wt %, about 90 wt %, or about 93 wt %. For example, the third effluent via line 132 can have a solvent concentration of from about 33 wt % to about 92 wt %, about 38 wt % to about 87 wt %, or about 43 wt % to about 82 wt %.

The third effluent via line 132 can be at ambient temperature. The third effluent via line 132 can have a pressure ranging from a low of about 720 kPa, about 740 kPa, about 760 kPa, or about 780 kPa to a high of about 800 kPa, about 820 kPa, about 840 kPa, or about 860 kPa. For example, the third effluent via line 132 can have a pressure of from about 730 kPa to about 850 kPa, about 750 kPa to about 830 kPa, or about 770 kPa to about 810 kPa. In another example, the third effluent via line 132 can have a pressure of about 785 kPa, about 790 kPa, or about 795 kPa.

The third effluent via line 132 and a hydrogen source via line 138 can be introduced to the one or more hydrogenators 140 to produce a fourth or "ethylene-rich" effluent or product via line 141. The one or more hydrogenators 140 can convert at least a portion of the acetylene in the third effluent introduced via line 132 to ethylene. For example, from about 95% to about 100% of the acetylene contained in the third effluent via line 132 can be converted to ethylene within the one or more hydrogenators 140.

The third effluent via line 132 can be combined with the hydrogen source via line 138 and a catalyst, not shown, in the one or more hydrogenators 140. The catalyst can be homogenous or heterogeneous. In one or more embodiments, the third effluent via line 132 can be hydrogenated without a catalyst. The catalysts in the one or more hydrogenators 140 can include, but is not limited to, catalysts containing nickel, palladium, and/or platinum as the active ingredient. The catalyst can be a metal catalyst or can be metal free.

The hydrogen source via line 138 can have a hydrogen concentration of about 90 mol % or more, about 95 mol % or more, about 99 mol % or more, or about 99.9 mol % or more. The hydrogen source can have a pressure ranging from a low of about 2,790 kPa, about 2,810 kPa, about 2,830 kPa, or about 2,850 kPa to a high of about 2,870 kPa, about 2,890 kPa, about 2,910 kPa, about 2,930 kPa. For example, the hydrogen source can have a pressure of from about 2,800 kPa to about 2,920 kPa, about 2,820 kPa to about 2,900 kPa, or about 2,840 kPa to about 2.980 kPa. In another example, the hydrogen source can have a pressure of about 2,860 kPa.

The fourth effluent via line 141 can include, but is not limited to, ethylene, ethane, methane, nitrogen, other trace components, or any combination thereof. The fourth effluent via line 141 can have an ethylene concentration ranging from a low of about 95.0 mol %, about 96.0 mol %, about 97.0 mol %, or about 98.0 mol % to a high of about 99.5 mol %, about 99.9 mol %, about 99.95 mol %, or about 99.99 mol %. For example, the fourth effluent via line 141 can have an ethylene concentration of from about 95.5 mol % to about 99.98 mol %, about 96.5 mol % to about 99.93 mol %, or about 97.5 mol % to about 99.75 mol %. The fourth effluent via line 141 can have a combined ethane, methane, and nitrogen concentration ranging from a low of about 0.01 mol %, about 0.05 mol %, about 0.1 mol %, or about 0.5 mol % to a high of about 2 mol %, about 3 mol %, about 4 mol %, or about 5 mol %. For example, the fourth effluent via line 141 can have a combined ethane, methane, and nitrogen concentration of from about 0.03 mol % to about 4.5 mol %, about 0.07 mol % to about 3.5 mol %, or about 0.3 mol % to about 2.5 mol %. Trace components in the fourth effluent via line 141 can include, but are not limited to, propylene, acetylene, hydrogen, carbon monoxide, carbon dioxide, water, oxygen, sulfur, methanol, ammonia, chlorides, carbonyls, or any combination thereof. Trace components in the fourth effluent via line 141 can be about 0.05 mol % or less, about 0.005 mol % or less, about 0.0005 mol % or less, or about 0.0002 mol % or less.

The fourth effluent via line 141, one or more butene sources via line 168, and one or more catalysts via line 169 can be introduced to the one or more metathesis reactors 170. The metathesis reactor 170 can catalytically react at least a portion of the ethylene in the ethylene-rich effluent introduced via line 141 with at least a portion of the butene in the butene source introduced via line 168 to produce a fifth or "propylene-rich" effluent via line 171. The metathesis reactor 170 can include one or more fixed beds, moving beds, fluidized beds, or a combination thereof. The metathesis reactor 170 can be adiabatic or isothermal.

The butene source via line 168 can include, but is not limited to, n-butane, isobutene, butene-1, butene-2, or any combination thereof. For example, the butene source via line 168 can have a n-butane concentration ranging from a low of about 0 wt %, about 1 wt %, or about 2 wt % to a high of about 3 wt %, about 4 wt %, or about 5 wt %. For example, the butene source via line 168 can have an n-butane concentration of about 0.5 wt % to about 4.5 wt % or about 1.5 wt % to about 3.5 wt %. The butene source via line 138 can have an isobutene concentration ranging from a low of about 0 wt %, about 4 wt %, about 8 wt %, or about 12 wt % to a high of about 18 wt %, about 22 wt %, about 26 wt %, or about 30 wt %. For example, the butene source via line 168 can have an isobutene concentration of about 2 wt % to about 28 wt %, about 6 wt % to about 24 wt %, or about 10 wt % to about 20 wt %. The butene source via line 138 can have a butene-1 concentration ranging from a low of about 20 wt %, about 25 wt %, about 30 wt %, or about 35 wt % to a high of about 45 wt %, about 50 wt %, about 55 wt %, or about 60 wt %. For example, the butene source via line 168 can have a butene-1 concentration of about 23 wt % to about 57 wt %, about 28 wt % to about 52 wt %, or about 33 wt % to about 47 wt %. The butene source via line 138 can have a butene-2 concentration ranging from a low of about 10 wt %, about 14 wt %, about 18 wt %, or about 22 wt % to a high of about 28 wt %, about 32 wt %, about 36 wt %, or about 40 wt %. For example, the butene source via line 168 can have a butene-2 concentration of about 12 wt % to about 38 wt %, about 16 wt % to about 34 wt %, or about 20 wt % to about 30 wt %.

Suitable catalysts via line 169 in the metathesis reactor 170 can include, but are not limited to, magnesium oxide, tungsten oxide, rhenium, or any combination thereof.

The fifth effluent via line 171 can include, but is not limited to, propylene, trace components, or any combination thereof. The fifth effluent via line 171 can have a propylene concentration ranging from a low of about 95.0 mol %, about 96.0 mol %, about 97.0 mol %, or about 98.0 mol % to a high of about 99.5 mol %, about 99.9 mol %, about 99.95 mol %, or about 99.99 mol %. For example, the fifth effluent via line 171 can have a propylene concentration of from about 95.5 mol % to about 99.98 mol %, about 96.5 mol % to about 99.93 mol %, or about 97.5 mol % to about 99.75 mol %. Trace components in the fifth effluent via line 171 can include, but are not limited to, ethylene, acetylene, hydrogen, carbon monoxide, carbon dioxide, water, oxygen, sulfur, methanol, ammonia, chlorides, carbonyls, or any combination thereof. Trace components in the fifth effluent via line 171 can be about 5 mol % or less, about 3 mol % or less, about 1 mol % or less, or about 0.01 mol % or less.

The metathesis reactor 170 can operate at a pressure ranging from a low about 2,850 kPa, about 2,950 kPa, about 3,050 kPa, or about 3,150 kPa to a high of about 3,250 kPa, about 3,350 kPa, about 3,450 kPa, or about 3,550 kPa. For example, the metathesis reactor 170 can operate at a pressure of about 2,900 kPa to about 3,500 kPa, about 3,000 kPa to about 3,400 kPa, or about 3,100 kPa to about 3,300 kPa.

Figure 2:
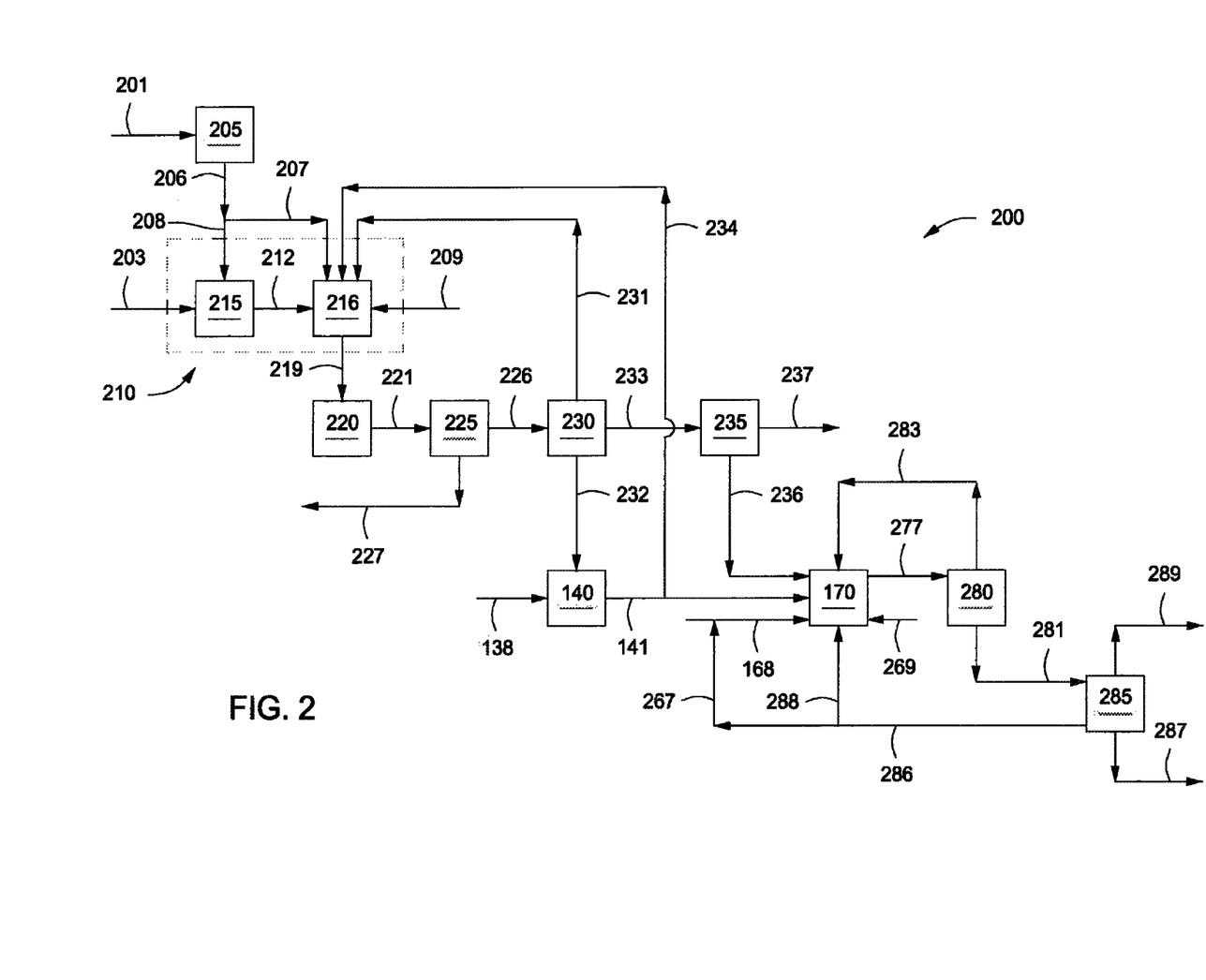
FIG. 2 depicts a schematic of another illustrative system for converting methane to propylene, according to one or more embodiments described.

FIG. 2 depicts a schematic of another illustrative system 200 for producing propylene, according to one or more embodiments. The system 200 can include one or more contaminant removal units 205, one or more first or "thermal" reactors 210 with one or more combustion sections 215 and one or more reaction sections 216, one or more quench sections 220, one or more carbon dioxide separators 225, one or more non-acetylene removal units 230, one or more ethylene separators 235, one or more hydrogenators 140, one or more metathesis reactors 170, one or more de-ethylenizers 280, and one or more de-propylenizers 285.

The one or more contaminant removal units 205 can be in fluid communications with the one or more first reactors 210 via at least lines 206. The one or more first reactors 210 can be in fluid communications with the one or more quench sections 220 via at least line 219. The one or more quench sections 220 can be in fluid communications with the one or more carbon dioxide separators 225 via at least line 221. The one or more carbon dioxide separators 225 can be in fluid communications with the one or more non-acetylene removal units 230 via at least line 226. The one or more non-acetylene removal units 230 can be in fluid communications with the one or more ethylene separators 235 via at least line 233. The one or more non-acetylene removal units 230 can be in fluid communications with the one or more hydrogenators 140 via at least line 232. The one or more ethylene separators 235 can be in fluid communications with the one or more metathesis reactors 170 via at least line 236. The one or more metathesis reactors 170 can be in fluid communications with the one or more de-ethylenizers 280 via at least line 277. The one or more de-ethylenizers 280 can be in fluid communications with the one or more de-propylenizers 285 via at least line 281.

A hydrocarbon via line 201 can be introduced to the one or more contaminant removal units 205 to produce a "contaminant-free" hydrocarbon via line 206 having a reduced concentration of impurities relative to the hydrocarbon via line 201. The hydrocarbon via line 201 can be at ambient temperature and pressure conditions and can include, but is not limited to, one or more $C_1$ to $C_{12}$ hydrocarbons, carbon dioxide, or any combination thereof. For example, the hydrocarbon via line 201 can include methane, ethane, propane, butane, pentane, hexane, carbon dioxide, $C_4$ or heavier hydrocarbons, or any combination thereof. The hydrocarbon via line 201 can have a methane concentration ranging from a low of about 75 mol %, about 77 mol %, about 79 mol %, or about 85 mol % to a high of about 90 mol %, about 96 mol %, about 98 mol %, or about 100 mol %. For example, the hydrocarbon via line 201 can have a methane concentration of from about 76 mol % to about 99 mol %, about 78 mol % to about 97 mol %, or about 80 mol % to about 95 mol %. The hydrocarbon via line 201 can have an ethane concentration ranging from a low of about 0 mol %, about 2 mol %, about 4 mol %, or about 6 mol % to a high of about 9 mol %, about 11 mol %, about 13 mol %, or about 15 mol %. For example, the hydrocarbon via line 201 can have an ethane concentration of from about 1 mol % to about 14 mol %, about 3 mol % to about 12 mol %, or about 5 mol % to about 10 mol %. The hydrocarbon via line 201 can have a propane concentration ranging from a low of about 0 mol %, about 2 mol %, or about 4 mol % to a high of about 6 mol %, about 8 mol %, or about 10 mol %. For example, the hydrocarbon via line 201 can have a propane concentration of from about 1 mol % to about 9 mol % or about 3 mol % to about 7 mol %. The hydrocarbon via line 201 can have a carbon dioxide concentration ranging from a low of about 0 mol %, about 2 mol %, about 4 mol %, or about 6 mol % to a high of about 9 mol %, about 11 mol %, about 13 mol %, or about 15 mol %. For example, the hydrocarbon via line 201 can have a carbon dioxide concentration of from about 1 mol % to about 14 mol %, about 3 mol % to about 12 mol %, or about 5 mol % to about 10 mol %. The hydrocarbon via line 201 can have from a low of about 0 mol %, about 2 mol %, or about 4 mol % to a high of about 6 mol %, about 8 mol %, or about 10 mol % $C_4$ or heavier hydrocarbons. For example, the hydrocarbon via line 201 can have of from about 1 mol % to about 9 mol %, about 3 mol % to about 7 mol %, or about 5 mol % to about 7 mol % $C_4$ or heavier hydrocarbons.

Illustrative contaminants or impurities that can be contained in the hydrocarbon via line 201 can include, but are not limited to, nitrogen, helium, hydrogen sulfide, water, mercury, sand, radon, organic sulfur, arsenic, organic oxygenates, nitric oxides, or any combination thereof. The hydrocarbon via line 201 can have a total contaminant concentration ranging from a low of about 10 parts per million (ppm) to a high of about 1 mol %.

The "contaminant-free" hydrocarbon via line 206 can include but is not limited to, one or more $C_1$ to $C_{12}$ hydrocarbons, hydrogen, or any combination thereof. For example, the hydrocarbon via line 206 can include methane, ethane, propane, butane, pentane, hexane, hydrogen, or any combination thereof. The composition of the "contaminant-free" hydrocarbon via line 206 can be the same as the hydrocarbon via line 201, but can be free from contaminants, e.g., the contaminants listed above. For example, the "contaminant-free" hydrocarbon via line 206 can have a total contaminant concentration of about 5 ppmv or less. The contaminant removal unit 205 may not completely remove all contaminants, as levels in the low ppm range for most contaminants can be tolerated in the downstream processes.

The hydrocarbon via line 206 can be divided or split into a first portion via line 208 and a second portion via line 207. The first portion via line 208 and one or more oxidants via line 203 can be introduced to one or more combustion sections 215 of the one or more first reactors 210 to produce a combustion gas via line 212. The oxidant via line 203 can come from any oxygen plant and can have a high purity. For example, the oxidant via line 203 can be about 99 mol % or more oxygen.

The combustion section 215 of the first reactor 210 can have a reaction temperature ranging from a low of about 700° C., about 725° C., or about 750° C. to a high of about 2,500° C., about 2,525° C., or about 2,550° C. Although not shown, water (e.g., liquid, gas, or any combination thereof) can be introduced to the combustion section 215 to lower and/or control the temperature of the combustion gas via line 212.

The combustion gas via line 212 can include, but is not limited to, one or more $C_1$ to $C_{12}$ hydrocarbons, hydrogen, or any combination thereof. For example, the combustion gas via line 212 can include methane, ethane, propane, butane, pentane, hexane, hydrogen, or any combination thereof. Depending on the configuration of the first reactor 210, the combustion gas via line 212 may not be isolatable.

The second portion via line 207, the combustion gas via line 212, and steam and/or nitrogen via line 209 can be introduced to one or more reaction sections 216 of the first reactor 210 to produce a first or "reacted" effluent via line 219. Although not shown, the second portion via line 207 to the reaction section 216 can be pre-heated in one or more pre-heaters and/or heated to a reaction temperature by direct heat exchange through combination with the combustion gas via line 212 from the combustion section 215. The reaction section 216 can have a reaction temperature ranging from a low of about 500° C., about 525° C., or about 550° C. to a high of about 2,500° C., about 2,525° C., or about 2,550° C.

The reaction temperature and/or pressure in the reaction section 216 can be adjusted to suppress production of undesirable components and increase production of acetylene and/or ethylene. For example, if the hydrocarbon via line 201 is "lean" natural gas, i.e., a gas with 95% or greater methane, the reaction section 216 can be operated at the upper end of the reaction temperature ranges discussed and described above to increase the content of alkynes, e.g., acetylene, produced in the reaction section 216. In another example, the pressure within the reaction section 216 can range from about 100 kPa to about 2000 kPa to increase production of acetylene and/or ethylene.

The reaction section 216 can have a residence time from ranging from about 0.1 milliseconds, about 1 millisecond, or about 5 milliseconds to a high of about 70 milliseconds, about 85 milliseconds, or about 100 milliseconds. For example, the residence time in the reaction section 216 can be about 0.5 milliseconds to about 95 milliseconds, about 0.5 milliseconds to about 80 milliseconds, about 1.5 milliseconds to about 90 milliseconds, or about 2.5 milliseconds to about 75 milliseconds. A residence time within this range in the reaction section 216 can minimize coke formation and can allow for conversion of the inlet feed effluent via line 207 into acetylene, ethylene, and/or other reactive compounds.

The first effluent via line 219 can include, but is not limited to, unconverted methane acetylene, hydrogen, carbon monoxide, carbon dioxide, water, or any combination thereof. The first effluent via line 219 can have a methane concentration ranging from a low of about 1 mol % to a high of about 10 mol %. The first effluent via line 219 can have an acetylene concentration ranging from a low of about 5 mol %, about 7 mol %, or about 9 mol % to a high of about 11 mol %, about 13 mol %, or about 15 mol %. For example, the effluent via line 219 can have an acetylene concentration of from about 6 mol % to about 14 mol % or about 8 mol % to about 12 mol %. The first effluent via line 219 can have a hydrogen concentration ranging from a low of about 20 mol %, about 25 mol %, or about 30 mol % to a high of about 40 mol %, about 45%, or about 50 mol %. For example, the first effluent via line 219 can have a hydrogen concentration of from about 23 mol % to about 47 mol %, about 26 mol % to about 44 mol %, or about 27 mol % to about 43 mol %. The first effluent via line 219 can have a carbon monoxide concentration ranging from a low of about 5 mol %, about 7 mol %, about 9 mol %, or about 11 mol % to a high of about 14 mol %, about 16 mol %, about 18 mol %, or about 20 mol %. For example, first effluent via line 219 can have a carbon monoxide concentration of from about 6 mol % to about 19 mol %, about 8 mol % to about 17 mol %, or about 10 mol % to about 15 mol %. The first effluent via line 219 can have a carbon dioxide concentration ranging from a low of about 1 mol %, about 2 mol %, or about 3 mol % to a high of about 4 mol % or about 5 mol %. The first effluent via line 219 can have a water concentration ranging from a low of about 30 mol %, about 32 mol %, about 34 mol %, or about 36 mol % to a high of about 44 mol %, about 46 mol %, about 48 mol %, or about 50 mol %. For example, first effluent via line 219 can have a water concentration of from about 31 mol % to about 49 mol %, about 33 mol % to about 47 mol %, or about 35 mol % to about 45 mol %. The first effluent via line 219 can have a nitrogen concentration of about 2 mol % or less or about 1 mol % or less. The first effluent via line 219 can have an oxygen concentration of about 2 mol % or less or about 1 mol % or less.

The first effluent via line 219 can have temperature of about 520° C. or more, about 525° C. or more, about 530° C. or more, about 535° C. or more, or about 540° C. or more. The first effluent via line 219 can have a pressure ranging from a low of about 135 kPa, about 140 kPa, about 145 kPa, or about 150 kPa to a high of about 155 kPa, about 160 kPa, about 165 kPa, or about 170 kPa. For example, the first effluent via line 219 can have a pressure of from about 137 kPa to about 168 kPa, about 143 kPa to about 162 kPa, or about 147 kPa to about 158 kPa.

The first effluent via line 219 can be introduced to the one or more quench sections 220 to produce a second or "quenched" effluent 221. The quench section 220 can be part of the first reactor 210 and/or can be a separate vessel, device, or component. The quench section 220 can quench the first effluent via line 219 by any methods known in the art including, but not limited to, one or more of spraying a quench fluid such as steam, water, oil, or liquid product into a reactor quench chamber; conveying the first effluent via 219 through or into water, natural gas feed, or liquid products; generating steam; or expanding first effluent via 219 in a kinetic energy quench, such as a Joule Thompson expander, choke nozzle, or turbo expander. Use of some quench fluids can induce further chemical reactions, possibly creating additional reactive hydrocarbon products, thereby increasing the overall energy and economic efficiency of the process, particularly when recovered or recycled effluents from downstream processing steps are used as the quench fluids. Quenching in the quench section 220 can be accomplished in multiple steps using different means, fluids, or both. The quench section can remove at least a portion of any water present in the first effluent via line 219.

The second effluent via line 221 can include methane, acetylene, hydrogen, carbon monoxide, carbon dioxide, water, or any combination thereof. The second effluent via line 221 can have the same composition as the first effluent via line 219, without most of the water. The second effluent via line 221 can have a methane concentration ranging from a low of about 1 mol % to a high of about 12 mol %. The second effluent via line 221 can have an acetylene concentration ranging from a low of about 5 mol %, about 7 mol %, about 9 mol %, or about 11 mol % to a high of about 19 mol %, about 21 mol %, about 23 mol %, or about 25 mol %. For example, the second effluent via line 221 can have an acetylene concentration of from about 6 mol % to about 24 mol %, about 8 mol % to about 22 mol %, or about 10 mol % to about 20 mol %. The second effluent via line 221 can have a hydrogen concentration ranging from a low of about 25 mol %, about 35 mol %, or about 45 mol % to a high of about 55 mol %, about 65%, or about 75 mol %. For example, the second effluent via line 221 can have a hydrogen concentration of from about 30 mol % to about 70 mol % or about 40 mol % to about 60 mol %. The second effluent via line 221 can have a carbon monoxide concentration ranging from a low of about 5 mol %, about 9 mol %, about 13 mol %, or about 17 mol % to a high of about 18 mol %, about 22 mol %, about 26 mol %, or about 30 mol %. For example, second effluent via line 221 can have a carbon monoxide concentration of from about 7 mol % to about 28 mol %, about 11 mol % to about 24 mol %, or about 15 mol % to about 20 mol %. The second effluent via line 221 can have a carbon dioxide concentration ranging from a low of about 1 mol %, about 2 mol %, or about 3 mol % to a high of about 6 mol %, about 7 mol %, or about 8 mol %. For example, the second effluent via line 221 can have a carbon dioxide concentration of from about 1.5 mol % to about 7.5 mol % or from about 2.5 mol % to about 6.5 mol %.

The second effluent via line 221 can have a nitrogen concentration of about 3 mol % or less, about 2 mol % or less, or about 1 mol % or less. The second effluent via line 221 can have an oxygen concentration of about 3 mol % or less, about 2 mol % or less, or about 1 mol % or less. The second effluent via line 221 can have a water concentration of about 10 mol % or less, about 8 mol % or less, about 6 mol % or less, about 4 mol % or less, about 2 mol % or less, or about 1 mol % or less.

A second effluent via line 221 from the quench section 220 can be introduced to the one or more carbon dioxide separators 225. The carbon dioxide separator 225 can separate at least a portion of any carbon dioxide from the second effluent via line 221 and/or from other locations within the process and produce a third or "carbon dioxide-lean" effluent via line 226 and a fourth or "carbon dioxide-rich" effluent via line 227. The carbon dioxide in the fourth effluent via 227 can be either removed from the process or recycled (not shown).

The third effluent via line 226 can include methane, acetylene, hydrogen, carbon dioxide, carbon monoxide, oxygen, nitrogen, water, or any combination thereof. The third effluent via line 226 can have a methane concentration ranging from a low of about 1 mol % to a high of about 15 mol %. The third effluent via line 226 can have an acetylene concentration ranging from a low of about 5 mol %, about 7 mol %, about 9 mol %, or about 11 mol % to a high of about 19 mol %, about 21 mol %, about 23 mol %, or about 25 mol %. For example, the third effluent via line 226 can have an acetylene concentration of from about 6 mol % to about 24 mol %, about 8 mol % to about 22 mol %, or about 10 mol % to about 20 mol %. The third effluent via line 226 can have a hydrogen concentration ranging from a low of about 25 mol %, about 35 mol %, or about 45 mol % to a high of about 60 mol %, about 70%, or about 80 mol %. For example, the third effluent via line 226 can have a hydrogen concentration of from about 30 mol % to about 75 mol % or about 40 mol % to about 65 mol %. The third effluent via line 226 can have a carbon monoxide concentration ranging from a low of about 5 mol %, about 9 mol %, about 13 mol %, or about 17 mol % to a high of about 18 mol %, about 22 mol %, about 26 mol %, or about 30 mol %. For example, third effluent via line 226 can have a carbon monoxide concentration of from about 7 mol % to about 28 mol %, about 11 mol % to about 24 mol %, or about 15 mol % to about 20 mol %. The third effluent via line 226 can have a nitrogen concentration of about 3 mol % or less, about 2 mol % or less, or about 1 mol % or less. The third effluent via line 226 can have an oxygen concentration of about 3 mol % or less, about 2 mol % or less, or about 1 mol % or less. The third effluent via line 226 can have a water concentration of about 10 mol % or less, about 8 mol % or less, about 6 mol % or less, about 4 mol % or less, about 2 mol % or less, or about 1 mol % or less. The third effluent via line 226 can have a carbon dioxide concentration of about 0.5 mol % or less, about 0.3 mol % or less, or about 0.1 mol % or less.

The fourth effluent via line 227 can include carbon dioxide, water, or any combination thereof. The fourth effluent via line 227 can have a carbon dioxide concentration ranging from a low of about 90 mol %, about 92 mol %, about 94 mol %, or about 95 mol % to a high of about 96 mol %, about 98 mol %, about 99.5 mol %, or about 99.99 mol %. For example, the carbon dioxide concentration can be of from about 91 mol % to about 99.9 mol %, about 93 mol % to about 99 mol %, or about 95 mol % to about 97 mol %. The carbon dioxide in the fourth effluent via line 227 can be saturated with water.

The third effluent via line 226 can be introduced to the one or more non-acetylene removal units 230. The non-acetylene removal unit 230 can separate acetylene from the third effluent via line 226 to produce a fifth or "acetylene-rich" effluent via line 232, a sixth or "acetylene-lean" effluents via lines 233, and a first or "acetylene-rich" recycle hydrocarbon via line 231. Separation in the non-acetylene removal unit 230 can be performed according to known methods including, but not limited to, absorption, distillation, selective membrane permeation, pressure swing absorption, or other separation techniques known in the art. The first recycle hydrocarbon via line 231 can be recycled to the reaction section 216 of the first reactor 210.

The fifth effluent via line 232 can include acetylene, methane, carbon dioxide, solvent, or any combination thereof. The acetylene in the fifth effluent via line 232 can be at least partially contained in the solvent. The fifth effluent via line 232 can have an acetylene concentration ranging from a low of about 5 wt %, about 10 wt %, about 15 wt %, or about 20 wt % to a high of about 35 wt %, about 40 wt %, about 45 wt %, or about 50 wt %. For example, the fifth effluent via line 232 can have an acetylene concentration of from about 7 wt % to about 48 wt %, about 12 wt % to about 43 wt %, or about 17 wt % to about 38 wt %. The fifth effluent via line 232 can have a methane concentration ranging from a low of about 1 wt %, about 3 wt %, or about 5 wt % to a high of about 6 wt %, about 8 wt %, or about 10 wt %. For example, the fifth effluent via line 232 can have a methane concentration of from about 2 wt % to about 9 wt % or about 4 wt % to about 7 wt %. The fifth effluent via line 232 can have a carbon dioxide concentration ranging from a low of about 1 wt %, about 3 wt %, or about 5 wt % to a high of about 6 wt %, about 8 wt %, or about 10 wt %. For example, the fifth effluent via line 232 can have a carbon dioxide concentration of from about 2 wt % to about 9 wt % or about 4 wt % to about 7 wt %. The fifth effluent via line 232 can have a solvent concentration ranging from a low of about 30 wt %, about 35 wt %, about 40 wt %, or about 45 wt % to a high of about 80 wt %, about 85 wt %, about 90 wt %, or about 93 wt %. For example, the fifth effluent via line 232 can have a solvent concentration of from about 33 wt % to about 92 wt %, about 38 wt % to about 87 wt %, or about 43 wt % to about 82 wt %.

The fifth effluent via line 232 can be at ambient temperature. The fifth effluent via line 232 can have a pressure ranging from a low of about 720 kPa, about 740 kPa, about 760 kPa, or about 780 kPa to a high of about 800 kPa, about 820 kPa, about 840 kPa, or about 860 kPa. For example, the fifth effluent via line 232 can have a pressure of from about 730 kPa to about 850 kPa, about 750 kPa to about 830 kPa, or about 770 kPa to about 810 kPa. In another example, the fifth effluent via line 232 can have a pressure of about 785 kPa, about 790 kPa, or about 795 kPa.

The sixth effluent via line 233 can include, but is not limited to, methane, acetylene, hydrogen, carbon monoxide, carbon dioxide, oxygen, nitrogen, $C_2$ hydrocarbons, or any combination thereof. The sixth effluent via line 233 can have a methane concentration ranging from a low of about 0 percent by weight (wt %) %, about 2 wt %, or about 4 wt % to a high of about 6 wt %, about 8 wt %, or about 10 wt %. For example, the sixth effluent via line 233 can have a methane concentration of from about 1 wt % to about 9 wt % or about 3 wt % to about 7 wt %. The sixth effluent via line 233 can have a carbon dioxide concentration ranging from a low of about 5 wt %, about 7 wt %, about 10 wt %, or about 13 wt % to a high of about 17 wt %, about 20 wt %, about 23 wt %, or about 25 wt %. For example, the sixth effluent via line 233 can have a carbon dioxide concentration of from about 6 wt % to about 24 wt %, about 8 wt % to about 22 wt %, or about 12 wt % to about 18 wt %. The sixth effluent via line 233 can have a nitrogen concentration ranging from a low of about 1 wt %, about 3 wt %, or about 5 wt % to a high of about 6 wt %, about 8 wt %, or about 10 wt %. For example, the sixth effluent via line 233 can have a nitrogen concentration of from about 2 wt % to about 9 wt % or about 4 wt % to about 7 wt %. The sixth effluent via line 233 can have a hydrogen concentration ranging from a low of about 5 wt %, about 7 wt %, or about 9 wt % to a high of about 11 wt %, about 13 wt %, or about 15 wt %. For example, the sixth effluent via line 233 can have a hydrogen concentration of from about 6 wt % to about 14 wt % or about 8 wt % to about 12 wt %. The sixth effluent via line 233 can have a carbon monoxide concentration ranging from a low of about 40 wt %, about 45 wt %, about 50 wt %, or about 55 wt % to a high of about 65 wt %, about 70 wt %, about 75 wt %, or about 80 wt %. For example, sixth effluent via line 233 can have a carbon monoxide concentration of from about 43 wt % to about 77 wt %, about 48 wt % to about 72 wt %, or about 53 wt % to about 67 wt %. The sixth effluent via line 233 can have an oxygen concentration of about 2 wt % or less or about 1 wt % or less. The sixth effluent via line 233 can include about 5 wt % or less, about 4 wt % or less, about 3 wt % or less, about 2 wt % or less, or about 1 wt % or less $C_2$ hydrocarbons.

The sixth effluent via line 233 can exit the non-acetylene removal unit 130 at ambient temperature and a low pressure. For example, the sixth effluent via line 233 can exit the non-acetylene removal unit 130 at a pressure ranging from a low of about 135 kPa, about 140 kPa, about 145 kPa, or about 150 kPa to a high of about 155 kPa, about 160 kPa, about 165 kPa, or about 170 kPa. In another example, the sixth effluent via line 233 can exit the non-acetylene removal unit 130 at a pressure of from about 137 kPa to about 168 kPa, about 143 kPa to about 162 kPa, or about 147 kPa to about 158 kPa.

The first recycle hydrocarbon via line 231 can include, but is not limited to, methane, hydrogen, acetylene, or any combination thereof. The first recycle hydrocarbon via line 231 can have a methane concentration ranging from a low of about 15 mol %, about 25 mol %, about 35 mol %, or about 45 mol % to a high of about 50 mol %, about 60 mol %, about 70 mol %, or about 80 mol %. For example, the first recycle hydrocarbon via line 231 can have a methane concentration of from about 20 mol % to about 75 mol %, about 30 mol % to about 65 mol %, or about 40 mol % to about 55 mol %. The first recycle hydrocarbon via line 231 can have a hydrogen concentration ranging from a low of about 15 mol %, about 25 mol %, about 35 mol %, or about 45 mol % to a high of about 50 mol %, about 60 mol %, about 70 mol %, or about 80 mol %. For example, the first recycle hydrocarbon via line 231 can have a hydrogen concentration of from about 20 mol % to about 75 mol %, about 30 mol % to about 65 mol %, or about 40 mol % to about 55 mol %. The first recycle hydrocarbon via line 231 can have an acetylene concentration ranging from a low of about 0.01 mol %, about 1 mol %, about 2 mol %, about 3 mol % to a high of about 7 mol %, about 8 mol %, about 9 mol %, or about 10 mol %. For example, the first recycle hydrocarbon via line 231 can have an acetylene concentration of from about 0.5 mol % to about 9.5 mol %, about 1.5 mol % to about 8.5 mol %, or about 2.5 mol % to about 7.5 mol %. In another example, the first recycle hydrocarbon via line 231 can have an acetylene concentration of about 6 mol % or less, about 5 mol % or less, or about 4 mol % or less.

The sixth effluent via line 233 can be introduced to the one or more ethylene separators 235. The ethylene separator 235 can separate ethylene from the sixth effluent via line 233 using known gas separation techniques to produce a seventh or "ethylene-rich" effluent via line 236 and an eighth or "ethylene-lean" effluent via line 237. Gas separation techniques can include, but are not limited to, conventional distillation, adsorption, absorption-distillation, or other gas separation techniques known in the art.

The seventh effluent via line 236 can include, but is not limited, ethylene and, possibly, some minor components, including, but not limited to, ethane, propane, or any combination thereof. The seventh effluent via line 236 can have an ethylene concentration of about 95 mol % or more, about 96 mol % or more, about 97 mol % or more, about 98 mol % or more, about 99 mol % or more, about 99.9 mol % or more, or about 99.99 mol % or more. The concentration of minor components, if present, in the seventh effluent via line 236 can be about 5 mol % or less, about 4 mol % or less, about 3 mol % or less, about 2 mol % or less, about 1 mol % or less, about 0.1 mol % or less, or about 0.01 mol % or less.

The eighth effluent via line 237 can include, but is not limited, ethylene, ethane, propane, or any combination thereof. The eighth effluent via line 237 can have an ethylene concentration ranging from a low of about 2 mol %, about 3 mol %, about 4 mol %, or about 5 mol % to a high of about 7 mol %, about 8 mol %, about 9 mol %, or about 10 mol %. For example, the eighth effluent via line 237 can have an ethylene concentration of about 2 mol % to about 9 mol %, about 3 mol % to about 8 mol %, or about 4 mol % to about 6 mol %. The eighth effluent via line 237 can have an ethane concentration ranging from a low of about 90 mol %, about 91 mol %, about 92 mol %, or about 93 mol % to a high of about 95 mol %, about 96 mol %, about 97 mol %, or about 98 mol %. Propane can be present in trace amounts in the eighth effluent via line 237. For example, the eighth effluent via line 237 can have a propane concentration of about 0.0002 mol % or less.

The fifth effluent via line 232 and a hydrogen source via line 138 can be introduced to the one or more hydrogenators 140 to produce a ninth or "ethylene-rich" effluent via line 141. The hydrogenation reactor 140 can also produce a recycle product via line 234. The recycle product via line 234 can be recycled to the reaction zone 216 of the reactor 210. As discussed and described above with reference to FIG. 1, the hydrogenation reactor 140 can produce the ethylene-rich effluent via line 141.

The hydrogen source via line 138 can have a hydrogen concentration of about 90 mol % or more, about 95 mol % or more, about 99 mol % or more, or about 99.9 mol % or more. The hydrogen source via line 138 can have a pressure ranging from a low of about 2,790 kPa, about 2,810 kPa, about 2,830 kPa, or about 2,850 kPa to a high of about 2,870 kPa, about 2,890, about 2,910, about 2,930 kPa. For example, the hydrogen source via line 138 can have a pressure of from about 2,800 kPa to about 2,920 kPa, about 2,820 kPa to about 2,900 kPa, or about 2,840 kPa to about 2,980 kPa. In another example, the hydrogen source can have a pressure of about 2,860 kPa.

The ninth effluent via line 141 can include, but is not limited to, ethylene, ethane, methane, nitrogen, other trace components, or any combination thereof. The ninth effluent via line 141 can have an ethylene concentration ranging from a low of about 95.0 mol %, about 96.0 mol %, about 97.0 mol %, or about 98.0 mol % to a high of about 99.5 mol %, about 99.9 mol %, about 99.95 mol %, or about 99.99 mol %. For example, the ninth effluent via line 141 can have an ethylene concentration of from about 95.5 mol % to about 99.98 mol %, about 96.5 mol % to about 99.93 mol %, or about 97.5 mol % to about 99.75 mol %. The ninth effluent via line 141 can have a combined ethane, methane, and nitrogen concentration ranging from a low of about 0.01 mol %, about 0.05 mol %, about 0.1 mol %, or about 0.5 mol % to a high of about 2 mol %, about 3 mol %, about 4 mol %, or about 5 mol %. For example, the ninth effluent via line 141 can have a combined ethane, methane, and nitrogen concentration of from about 0.03 mol % to about 4.5 mol %, about 0.07 mol % to about 3.5 mol %, or about 0.3 mol % to about 2.5 mol %. Trace components in the ninth effluent via line 141 can include, but are not limited to, propylene, acetylene, hydrogen, carbon monoxide, carbon dioxide, water, oxygen, sulfur, methanol, ammonia, chlorides, carbonyls, or any combination thereof. Trace components in the ninth effluent via line 141 can be about 0.0002 mol % or less.

A butene source via line 168, the ninth effluent via line 141 and/or the seventh effluent via line 236, and one or more catalysts via line 269 can be introduced to the one or more metathesis reactors 170 to produce a tenth or "propylene-rich" effluent via line 277. Although not shown, the ninth effluent via line 141 and the seventh effluent via line 236 can be combined prior to their introduction to the metathesis reactor 170. The butene source via line 168, the ethylene rich effluent via line 141, and/or the ethylene rich effluent via line 236 can be introduced to the bottom of the metathesis reactor 170.

The butene source via line 168 can include, but is not limited to, n-butane, isobutene, butene-1, butene-2, or any combination thereof. For example, the butene source via line 168 can have a n-butane concentration ranging from a low of about 0.01 wt %, about 1 wt %, or about 2 wt % to a high of about 3 wt %, about 4 wt %, or about 5 wt %. For example, the butene source via line 168 can have a n-butane concentration of about 0.5 wt % to about 4.5 wt % or about 1.5 wt % to about 3.5 wt %. The butene source via line 138 can have an isobutene concentration ranging from a low of about 0.01 wt %, about 4 wt %, about 8 wt %, or about 12 wt % to a high of about 18 wt %, about 22 wt %, about 26 wt %, or about 30 wt %. For example, the butene source via line 168 can have an isobutene concentration of about 2 wt % to about 28 wt %, about 6 wt % to about 24 wt %, or about 10 wt % to about 20 wt %. The butene source via line 138 can have a butene-1 concentration ranging from a low of about 20 wt %, about 25 wt %, about 30 wt %, or about 35 wt % to a high of about 45 wt %, about 50 wt %, about 55 wt %, or about 60 wt %. For example, the butene source via line 168 can have a butene-1 concentration of about 23 wt % to about 57 wt %, about 28 wt % to about 52 wt %, or about 33 wt % to about 47 wt %. The butene source via line 138 can have a butene-2 concentration ranging from a low of about 10 wt %, about 14 wt %, about 18 wt %, or about 22 wt % to a high of about 28 wt %, about 32 wt %, about 36 wt %, or about 40 wt %. For example, the butene source via line 168 can have a butene-2 concentration of about 12 wt % to about 38 wt %, about 16 wt % to about 34 wt %, or about 20 wt % to about 30 wt %.

In one or more embodiments, the catalyst via line 269 can be a slurry and can be introduced to the top of the metathesis reactor 170. Suitable catalysts for the metathesis reactor 170 can include, but are not limited to, magnesium oxide, tungsten oxide, rhenium, or any combination thereof.

The tenth effluent via line 277 can include propylene and, possibly, some minor components, including, but not limited to, ethylene, ethane, propane, or any combination thereof. The tenth effluent via line 277 can have an propylene concentration of about 95 mol % or more, about 96 mol % or more, about 97 mol % or more, about 98 mol % or more, about 99.9 mol % or more, or about 99.99 mol % or more. The concentration of minor components, if present, in the tenth effluent via line 277 can be about 5 mol % or less, about 4 mol % or less, about 3 mol % or less, about 2 mol % or less, about 1 mol % or less, about 0.1 mol % or less, or about 0.01 mol % or less.

The tenth effluent via line 277 can be introduced to the one or more de-ethylenizers 280. The de-ethylenizer 280 can separate at least a portion of any unreacted ethylene from tenth effluent via line 277 to produce an eleventh or "purified propylene-rich" effluent via line 281 and a second or "ethylene-rich" recycle hydrocarbon via line 283. The second recycle hydrocarbon via line 283 can be recycled to the metathesis reactor 170.

The eleventh effluent via line 281 can include propylene and, possibly, trace elements. The eleventh effluent via line 281 can have a propylene concentration of about 95 mol % or more, about 97 mol % or more, about 99 mol % or more, about 99.9 mol % or more, or about 99.99 mol % or more. Trace components in the eleventh effluent via line 281 can be about 0.001 mol % or less.

The second recycle hydrocarbon via line 283 can include ethylene and, possibly, some minor components, including, but not limited to, propylene, ethane, propane, or any combination thereof. The second recycle hydrocarbon via line 283 can have an ethylene concentration of about 95 mol % or more, about 96 mol % or more, about 97 mol % or more, about 98 mol % or more, about 99 mol % or more, about 99.9 mol % or more, or about 99.99 mol % or more. The concentration of minor components, if present, in the second recycle hydrocarbon via line 283 can be about 5 mol % or less, about 4 mol % or less, about 3 mol % or less, about 2 mol % or less, about 1 mol % or less, about 0.1 mol % or less, or about 0.01 mol % or less.

The eleventh effluent via line 281 can be introduced to the one or more de-propylenizers 285. At least a portion of any butenes and any heavier hydrocarbons, i.e., $C_4$ and heavier, can be separated from the eleventh effluent via line 281 in the de-propylenizer 285 to produce a first or "propylene-rich" product via line 289, a twelfth or "butene-rich" effluent via line 286, and a second product via bottoms 287 containing $C_4$ and heavier hydrocarbons. The twelfth effluent via line 286 can be recycled via line 267 back to the butene source via line 168 and/or can be recycled via line 288 directly to the metathesis reactor 170 to provide butene for the metathesis reaction therein.

The twelfth effluent via line 286 can include propylene, isobutene, butene-1, butene-2, or any combination thereof. The twelfth effluent via line 286 can have a propylene concentration ranging from a low of about 0.01 mol %, about 2 mol %, or about 4 mol % to a high of about 6 mol %, about 8 mol %, or about 10 mol %. For example, the twelfth effluent via line 286 can have a propylene concentration of from about 1 mol % to about 9 mol % or about 3 mol % to about 7 mol %. The twelfth effluent via line 286 can have an isobutene concentration ranging from a low of about 0.01 mol %, about 4 mol %, about 8 mol %, or about 12 mol % to a high of about 18 mol %, about 22 mol %, about 26 mol %, or about 30 mol %. For example, the twelfth effluent via line 286 can have an isobutene concentration of about 2 mol % to about 28 mol %, about 6 mol % to about 24 mol %, or about 10 mol % to about 20 mol %. The twelfth effluent via line 286 can have a butene-1 concentration ranging from a low of about 20 mol %, about 25 mol %, about 30 mol %, or about 35 mol % to a high of about 45 mol %, about 50 mol %, about 55 mol %, or about 60 mol %. For example, the twelfth effluent via line 286 can have a butene-1 concentration of about 23 mol % to about 57 mol %, about 28 mol % to about 52 mol %, or about 33 mol % to about 47 mol %. The twelfth effluent via line 286 can have a butene-2 concentration ranging from a low of about 10 mol %, about 14 mol %, about 18 mol %, or about 22 mol % to a high of about 28 mol %, about 32 mol %, about 36 mol %, or about 40 mol %. For example, the twelfth effluent via line 286 can have a butene-2 concentration of about 12 mol % to about 38 mol %, about 16 mol % to about 34 mol %, or about 20 mol % to about 30 mol %.

The first product via line 289 can include propylene and, possibly, trace elements. The first product via line 289 can have a propylene concentration of about 95 mol % or more, about 97 mol % or more, about 99 mol % or more, about 99.9 mol % or more, or about 99.99 mol % or more. Trace components in the first product via line 289 can be about 0.001 mol % or less.

The second product via bottoms 287 can include butenes, $C_5$ hydrocarbons and heavier, or any combination thereof. The second product via bottoms 287 can have a butenes concentration ranging from a low of about 75 mol %, about 77 mol %, about 79 mol %, or about 81 mol % to a high of about 84 mol %, about 86 mol %, about 88 mol %, or about 90 mol %. For example, the second product via bottoms 287 can have a butenes concentration of from about 76 mol % to about 89 mol %, about 78 mol % to about 87 mol %, or about 80 mol % to about 85 mol %. The second product via bottoms 287 can have from a low of about 0 mol %, about 2 mol %, or about 4 mol % to a high of about 6 mol %, about 8 mol %, or about 10 mol % $C_5$ or heavier hydrocarbons. For example, the second product via bottoms 287 can have of from about 1 mol % to about 9 mol %, about 3 mol % to about 7 mol %, or about 5 mol % to about 7 mol % $C_5$ or heavier hydrocarbons.

Prophetic Example

The foregoing discussion can be further described with reference to the following non-limiting prophetic example. The system 100, according to one or more embodiments discusses and described above, operates to produce propylene from a natural gas containing hydrocarbon source or natural gas. Natural gas having a methane concentration of 90 mol %, an ethane concentration of 1 mol %, a propane concentration of about 2 mol %, a carbon dioxide concentration of about 3 mol %, and a C4 or heavier hydrocarbon concentration of about 4 mol % is introduced into the reactor 110 for cracking. The resultant first product includes acetylene, hydrogen, carbon monoxide, carbon dioxide, water, or any combination thereof.

From the first product, acetylene is isolated in the non-acetylene removal unit 130. The isolated acetylene is converted to a second product, including ethylene, in the hydrogenator 140. The ethylene rich second product from the hydrogenator 140 is introduced into the metathesis reactor 170 for catalytically reacting the ethylene with one or more butene products to produce a third product comprising propylene. The resultant third product can have a propylene concentration of up to 95.0 mol % or more. The resultant propylene can be used in other processes, can be transported to other locations for storage or use, or can be stored in-situ for later use.

Embodiments of the present disclosure further relate to any one or more of the following numbered paragraphs 1 through 20:

1. A method for processing a hydrocarbon, comprising thermally converting a hydrocarbon comprising methane to produce a first product comprising acetylene; hydrogenating the first product to produce a second product comprising ethylene; and catalytically reacting the second product with one or more butene products to produce a third product comprising propylene.

2. The method of paragraph 1, wherein the propylene product comprises about 95 mol % or more propylene.

3. The method of paragraph 1 or 2, wherein the hydrocarbon comprises from about 75 mol % to about 100 mol % methane.

4. The method according to any one of paragraphs 1 to 3, further comprising removing non-acetylene from the first product to produce an acetylene-rich product; and hydrogenating the acetylene-rich product to produce the second product.

5. The method of paragraph 4, wherein the acetylene-rich product comprises from about 5 wt % to about 50 wt % acetylene.

6. The method according to any one of paragraphs 1 to 5, wherein the one or more butene products comprise butene-1 and butene-2.

7. The method of paragraph 6, wherein the butene products further comprise n-butane and isobutene.

8. A method for processing a hydrocarbon, comprising introducing a hydrocarbon comprising methane to a reactor to thermally convert at least a portion of the hydrocarbon to produce a first product comprising acetylene; introducing the first product to a non-acetylene removal unit to produce an acetylene-rich effluent and an acetylene-lean effluent; introducing the acetylene-rich effluent and a hydrogen source to a hydrogenation reactor to hydrogenate at least a portion of the acetylene in the acetylene-rich product to produce a second product comprising ethylene; and introducing the second product and butene to a metathesis reactor to catalytically react at least a portion of the ethylene in the second product with at least a portion of the butene to produce a third product comprising propylene.

9. The method of paragraph 8, wherein the acetylene-rich product comprises from about 5 wt % to about 50 wt % acetylene.

10. The method of paragraph 8 or 9, wherein the first product comprises carbon dioxide, water, hydrogen, carbon monoxide, and acetylene.

11. The method of claim 10, wherein the first product comprises from about 5 mol % to about 15 mol % acetylene.

12. The method according to any one of paragraphs 8 to 11, wherein the third product comprises about 95 mol % or more propylene.

13. The method according to any one of paragraphs 8 to 12, wherein the hydrogenation reactor produces a recycle product, wherein the recycle product is recycled to the reactor.

14. The method according to any one of paragraphs 8 to 13, further comprising introducing the acetylene-lean product to an ethylene separator to produce an ethylene-rich product and an ethylene-lean product.

15. A system for processing a hydrocarbon, comprising one or more thermal reactors adapted to convert a hydrocarbon comprising methane to produce a first product comprising acetylene; one or more hydrogenation reactors adapted to hydrogenate at least a portion of the acetylene in the first product to produce a second product comprising ethylene; and one or more metathesis reactors adapted to catalytically react at least a portion of the ethylene in the second product with a butene source to produce a third product comprising propylene.

16. The system of paragraph 15, wherein the first product further comprises carbon dioxide, water, hydrogen, and carbon monoxide.

17. The system of paragraph 16, further comprising a non-acetylene removal unit adapted to remove at least a portion of the non-acetylene components of the first product.

18. The system of paragraph 16 or 17, further comprising a quench section adapted to remove at least a portion of the water in the first product.

19. The system according to any one of paragraphs 16 to 18, further comprising a carbon dioxide separator adapted to remove at least a portion of the carbon dioxide in the first product.

20. The system according to any one of paragraphs 15 to 19, further comprising a de-ethylenizer adapted to separate at least a portion of any unreacted ethylene from the third product and produce a fourth product and a recycle comprising ethylene, wherein the fourth product comprises propylene; and a de-propylenizer adapted to separate at least a portion of any butenes and any $C_4$ or heavier hydrocarbons from the fourth product to produce a fifth product comprising propylene and a sixth product comprising butenes and $C_4$ or heavier hydrocarbons.

Certain embodiments and features have been described using a set of numerical upper limits and a set of numerical lower limits. It should be appreciated that ranges from any lower limit to any upper limit are contemplated unless otherwise indicated. Certain lower limits, upper limits, and ranges appear in one or more claims below. All numerical values are "about" or "approximately" the indicated value, and take into account experimental error and variations that would be expected by a person having ordinary skill in the art. It is assumed that the sum of all percents (whether weight, volume, mol or otherwise) of components of a single stream equal to 100% unless otherwise stated.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present disclosure, other and further embodiments of the disclosure may be devised without departing from the basic scope thereof, and the scope thereof is determined by the claims that follow.

What is claimed is:

1. A method for processing a hydrocarbon, comprising:
    thermally converting a hydrocarbon comprising methane to produce a first product comprising acetylene;
    hydrogenating the first product to produce a second product comprising ethylene; and
    catalytically reacting the second product with a butene product comprising about 4 wt % to about 30 wt % isobutene, about 0.5 wt % to about 4.5 wt % n-butane, about 20 wt % to about 45 wt % butene-1, and about 12 wt % to about 38 wt % butene-2 in a metathesis reactor to produce a third product comprising propylene, wherein the third product, upon exiting the metathesis reactor and prior to any further treatment, comprises about 95 mol % or more propylene.

2. The method of claim 1, wherein the butene product comprises about 18 wt % to about 30 wt % isobutene.

3. The method of claim 1, wherein the hydrocarbon comprises from about 75 mol % to about 100 mol % methane.

4. The method of claim 1, further comprising:
    removing non-acetylene from the first product to produce an acetylene-rich product; and
    hydrogenating the acetylene-rich product to produce the second product.

5. The method of claim 4, wherein the acetylene-rich product comprises from about 5 wt % to about 50 wt % acetylene.

6. The method of claim 1, wherein the metathesis reactor comprises a rhenium containing catalyst.

7. The method of claim 1, wherein the metathesis reactor comprises a magnesium oxide containing catalyst.

8. A method for processing a hydrocarbon, comprising:
    introducing a hydrocarbon comprising methane to a reactor to thermally convert at least a portion of the hydrocarbon to produce a first product comprising acetylene;
    introducing the first product to a non-acetylene removal unit to produce an acetylene-rich effluent and an acetylene-lean effluent;
    introducing the acetylene-rich effluent and a hydrogen source to a hydrogenation reactor to hydrogenate at least a portion of the acetylene in the acetylene-rich effluent to produce a second product comprising ethylene; and
    introducing the second product and a butene product comprising about 4 wt % to about 30 wt % isobutene, about 0.5 wt % to about 4.5 wt % n-butane about 20 wt % to about 45 wt % butene-1, and about 12 wt % to about 38 wt % butene-2 to a metathesis reactor to catalytically react at least a portion of the ethylene in the second product with at least a portion of the butene product to produce a third product comprising propylene, wherein the third product, upon exiting the metathesis reactor and prior to any further treatment, comprises about 95 mol % or more propylene.

9. The method of claim 8, wherein the acetylene-rich effluent comprises from about 5 wt % to about 50 wt % acetylene.

10. The method of claim 8, wherein the first product comprises carbon dioxide, water, hydrogen, carbon monoxide, and acetylene.

11. The method of claim 10, wherein the first product comprises from about 5 mol % to about 15 mol % acetylene.

12. The method of claim 8, wherein the third product comprises about 97 mol % or more propylene.

13. The method of claim 8, wherein the hydrogenation reactor produces a recycle product, wherein the recycle product is recycled to the reactor.

14. The method of claim 8, further comprising introducing the acetylene-lean effluent to an ethylene separator to produce an ethylene-rich product and an ethylene-lean product.

15. The method of claim 1, wherein hydrogenation of the first product further produces a recycle product, and wherein the recycle product is thermally converted.

16. The method of claim 1, wherein the second product comprises from about 95 mol % to about 99.99 mol % ethylene.

17. The method of claim 1, the metathesis reactor comprises a tungsten oxide containing catalyst.

18. The method of claim 1, wherein the hydrocarbon is thermally converted in a reactor comprising a combustion section and a reaction section, the method further comprising:
    removing non-acetylene from the first product to produce an acetylene-rich product and a recycle product;
    introducing the recycle product to the reaction section; and
    hydrogenating the acetylene-rich product to produce the second product comprising ethylene.

19. The method of claim 18, wherein the recycle product comprises about 15 mol % to about 80 mol % methane and about 3 mol % to about 10 mol % acetylene, and wherein the acetylene-rich product comprises about 1 wt % to about 10 wt % methane and about 5 wt % to about 50 wt % acetylene.

20. The method of claim 1, wherein the butene product comprises about 12 wt % to about 30 wt % isobutene.

* * * * *